(12) United States Patent
Henning et al.

(10) Patent No.: US 9,005,361 B2
(45) Date of Patent: Apr. 14, 2015

(54) DEFOAMER COMPOSITIONS FOR BUILDING-PRODUCT MIXTURES

(71) Applicants: Frauke Henning, Essen (DE); Anke Reinschmidt, Essen (DE); Ralph Scheuermann, Essen (DE); George-Hans Bayne, Essen (DE); Kerstin Klein, Duisburg (DE); Markus Roos, Essen (DE)

(72) Inventors: Frauke Henning, Essen (DE); Anke Reinschmidt, Essen (DE); Ralph Scheuermann, Essen (DE); George-Hans Bayne, Essen (DE); Kerstin Klein, Duisburg (DE); Markus Roos, Essen (DE)

(73) Assignee: Evonik Industries AG, Essen (DE)

( * ) Notice: Subject to any disclaimer, the term of this patent is extended or adjusted under 35 U.S.C. 154(b) by 0 days.

(21) Appl. No.: 13/719,791

(22) Filed: Dec. 19, 2012

(65) Prior Publication Data

US 2013/0174760 A1 Jul. 11, 2013

(30) Foreign Application Priority Data

Dec. 22, 2011 (DE) .......................... 10 2011 089 535

(51) Int. Cl.
| | | |
|---|---|---|
| *C08G 77/46* | (2006.01) | |
| *C04B 24/42* | (2006.01) | |
| *C08L 83/12* | (2006.01) | |
| *C07F 7/08* | (2006.01) | |
| *C04B 28/02* | (2006.01) | |
| *C04B 28/14* | (2006.01) | |
| *C04B 103/50* | (2006.01) | |

(52) U.S. Cl.
CPC ................ *C04B 24/42* (2013.01); *C08G 77/46* (2013.01); *C08L 83/12* (2013.01); *C07F 7/0896* (2013.01); *C04B 28/02* (2013.01); *C04B 28/14* (2013.01); *C04B 2103/50* (2013.01)

(58) Field of Classification Search
USPC ............................. 106/806; 556/445; 524/588
See application file for complete search history.

(56) References Cited

U.S. PATENT DOCUMENTS

| | | | |
|---|---|---|---|
| 7,619,035 B2 | 11/2009 | Henning et al. | |
| 7,931,747 B2 | 4/2011 | Weyershausen et al. | |
| 8,138,294 B2 | 3/2012 | Henning et al. | |
| 8,268,939 B2 | 9/2012 | Ebbrecht et al. | |
| 8,283,422 B2 | 10/2012 | Schubert et al. | |
| 8,309,664 B2 | 11/2012 | Knott et al. | |
| 8,334,355 B2 | 12/2012 | Henning et al. | |
| 8,349,907 B2 | 1/2013 | Henning et al. | |
| 2007/0006779 A1* | 1/2007 | Zampini et al. ............... 106/806 |
| 2007/0144406 A1* | 6/2007 | Zampini ....................... 106/806 |
| 2008/0004357 A1 | 1/2008 | Meyer et al. | |
| 2008/0125503 A1 | 5/2008 | Henning et al. | |
| 2009/0305019 A1* | 12/2009 | Chanvillard et al. ......... 428/220 |
| 2010/0022435 A1 | 1/2010 | Henning et al. | |
| 2010/0029587 A1 | 2/2010 | Brückner et al. | |
| 2010/0041629 A1 | 2/2010 | Giessler-Blank et al. | |
| 2010/0056649 A1* | 3/2010 | Henning et al. ............... 521/25 |
| 2010/0081781 A1 | 4/2010 | Schubert et al. | |
| 2010/0113633 A1 | 5/2010 | Henning et al. | |
| 2010/0186870 A1 | 7/2010 | Stuart et al. | |
| 2010/0249339 A1 | 9/2010 | Henning et al. | |
| 2010/0298455 A1 | 11/2010 | Henning et al. | |
| 2011/0021693 A1 | 1/2011 | Henning et al. | |
| 2011/0172373 A1 | 7/2011 | Knott et al. | |
| 2011/0306694 A1 | 12/2011 | Glos et al. | |
| 2012/0027704 A1 | 2/2012 | Henning et al. | |
| 2012/0046486 A1 | 2/2012 | Henning et al. | |
| 2012/0097883 A1 | 4/2012 | Henning et al. | |
| 2012/0190760 A1 | 7/2012 | Henning et al. | |
| 2012/0190762 A1 | 7/2012 | Hubel et al. | |
| 2012/0282210 A1 | 11/2012 | Henning et al. | |
| 2012/0308494 A1 | 12/2012 | Schubert et al. | |

FOREIGN PATENT DOCUMENTS

| | | |
|---|---|---|
| DE | 10 2010 029 588 A1 | 12/2011 |
| EP | 2 107 077 A1 | 10/2009 |
| EP | 2 159 248 A1 | 3/2010 |
| EP | 2 182 020 A1 | 5/2010 |

OTHER PUBLICATIONS

Extended European Search Report issued Apr. 26, 2013 in Patent Application No. 12195982.9 with English translation of categories of cited documents.

* cited by examiner

*Primary Examiner* — Margaret Moore

(74) *Attorney, Agent, or Firm* — Oblon, McClelland, Maier & Neustadt, L.L.P.

(57) ABSTRACT

The present application relates to compositions comprising at least one siloxane and at least one superplasticizer based on polycarboxylate ethers or sulphonates of lignin, melamine or naphthalene or of resins thereof, and to the use of such compositions as or in building-product mixtures or building products, especially mortar mixtures or concrete mixtures. Preferably the siloxane is a branched siloxane containing at least one "T" unit and containing at least two different polyoxyalkylene moieties.

20 Claims, No Drawings

DEFOAMER COMPOSITIONS FOR BUILDING-PRODUCT MIXTURES

FIELD OF THE INVENTION

The invention relates to defoamer compositions for building-product mixtures, which have good compatibility with superplasticizers, especially with polar superplasticizers.

DISCUSSION OF THE BACKGROUND

Building-product mixtures, especially concrete and mortar mixtures, are frequently modified with rheology-control additives to keep the mixture flowable and hence efficiently workable. These additives, which are also called superplasticizers, are described in the art and are usually based on polycarboxylate ethers or sulphonates of lignin (resins), melamine (resins) or (poly)naphthalene (resins), and are usually added in aqueous solution to the building-product mixture at the mixing stage. A disadvantage with the use of superplasticizers is the higher entrapment of air into the building-product mixture and hence also in the hardening concrete and mortar. This can lead to deficiencies of mechanical strength and weatherability. Therefore, defoamers or deaerators are often admixed as further additives in order that air entrapment may be reduced.

Defoamers used in the art have the disadvantage that they are frequently water-insoluble and hence do not become distributed uniformly in the aqueous systems. A mixed-additive formulation comprising a superplasticizer and a defoamer is frequently a cloudy mixture which, in relatively short order, can phase-separate between the polar superplasticizer and the apolar, interface-occupatory defoamer. Even worse, an emulsion may not even be formulatable in the first place.

The art does not disclose any siloxane-based water-soluble defoamer for hydraulically hardenable building products which is miscible with superplasticizers in the relevant concentration range and which does not divide into separable phases.

The problem addressed by the present invention was therefore that of providing water-soluble compounds which are useful as defoamers in hydraulically hardenable building products and have good compatibility with superplasticizers.

It was found that, surprisingly, this problem is solved by water-soluble siloxanes having at least two different polyalkoxylene moieties.

This is an unforeseeable surprise to a person skilled in the art particularly because hydrophilic organomodified siloxanes tend to be used more for foam stabilization than for defoaming, as described for example in patent application DE 10 2008 043343.8 (US 2010 0113633 A1).

SUMMARY OF THE INVENTION

The present invention accordingly provides compositions comprising at least one siloxane of formula (I) and one or more superplasticizers based on polycarboxylate ethers and/or sulphonates of lignin, melamine or naphthalene or of resins thereof.

The present invention likewise provides for the use of siloxanes of formula (I) or compositions comprising at least one siloxane of formula (I) and also one or more superplasticizers in or for production of building-product mixtures and their use, especially as defoamers, and also the corresponding building-product materials.

DETAILED DESCRIPTION OF THE PREFERRED EMBODIMENTS

The use according to the present invention of siloxanes of formula (I) for production of building-product mixtures has the advantage that these siloxanes have good compatibility with the superplasticizers which are typically used. The good compatibility with the superplasticizers ensures that compositions which include the siloxanes of formula (I) as well as superplasticizers have relatively prolonged stability, if stability is to be understood as meaning that the compositions of the present invention are optically transparent and/or the components do not, within 90 days at 25° C., separate such that these components are present in two phases that have only one common interphasial boundary. Emulsions where there are two phases but two or more interphasial boundaries are considered to be stable for the purposes of the present invention.

One result of the good compatibility and stability is the absence of concentration gradients along the height dimension of a storage vessel. This ensures that compositions having identical concentration ratios are at all times removable from the vessel even on prolonged storage and with the fill level varying in the vessel.

A further advantage of compositions according to the present invention is in their good defoaming performance.

To assess the foaming behaviour of aqueous solutions of the defoamers (as listed in table 4 for example) and of superplasticizer blends (as listed in table 5), the mixtures in question can be shaken. Foam degradation can be observed over time.

The compositions of the present invention or the siloxanes of formula (I) provide very good deaeration in building-product mixtures such as concrete or mortar mixtures. The building-product mixtures using the preparations of the present invention further had high slump.

A further advantage of compositions which are in accordance with the present invention in that they comprise one or more siloxanes of formula (I) and one or more superplasticizers is in their low toxicity due to siloxanes of formula (I), since these are polymers, so any resorption is distinctly reduced compared with low molecular weight materials. For example, one defoamer often employed with PCE superplasticizers is tributyl phosphate (CAS RN 126-73-8; e.g. from Lanxess Deutschland GmbH or Merck KGaA), which bears the H- and P-sentences H: 351-302-315 and P: 281-302+350-308+313. Similarly, the frequently used triisobutyl phosphate (CAS RN 126-71-6; likewise for example from Lanxess Deutschland GmbH or Merck KGaA) cannot be regarded as an unconcerning alternative (H: 317-412 and P: P262-273-280-302+352), so the compounds of the present invention represent a distinct improvement, especially against the background of typical building-site safety measures for storing/handling the materials.

It may be advantageous for the compositions of the present invention, which comprise one or more siloxanes of formula (I) and one or more superplasticizers, to further comprise water.

The compositions of the present invention, which comprises one or more siloxanes of formula (I) and one or more superplasticizers based on polycarboxylate ethers and/or sulphonates of lignin, melamine or naphthalene or of resins thereof, and also their uses in or for production of building-product mixtures and their use particularly as defoamers and/or as deaerators will now be described by way of example without any intention to restrict the invention to these exemplary embodiments. When ranges, general formulae or classes of compounds are recited hereinbelow, these shall encompass not just the corresponding ranges or groups of compounds explicitly mentioned, but also sub-ranges and sub-groups of compounds obtainable by removing individual values (ranges) or compounds. Averages recited hereinbelow are number averages, unless otherwise stated. Molar masses used are weight-average molar masses Mw, unless explicitly stated otherwise. Contents recited hereinabove or hereinbelow (as ppm or %) are % by weight or weight ppm, unless otherwise stated. Contents recited for compositions are based on the overall composition, unless otherwise stated. Measurements recited hereinbelow were determined at a temperature of 25° C. and a pressure of 1013 mbar, unless otherwise stated.

The compositions of the present invention comprises at least one organomodified siloxane of formula (I)

$$M_{a1}M^A{}_{a2}M^B{}_{a3}M^C{}_{a4}D_{b1}D^A{}_{b2}D^B{}_{b3}D^C{}_{b4}T_{c1}T^A{}_{c2}T^B{}_{c3}T^C{}_{c4}Q_{d1} \quad \text{(Formula I)}$$

where
a1=0 to 32; preferably 0 to 22, especially above 0 to 12;
a2=0 to 10, preferably 0 to 5, especially 0;
a3=0 to 32; preferably above 0 to 22, especially 1 to 12;
a4=0 to 10; preferably 0 to 5, especially 0;
b1=1 to 600, preferably 10 to 500, especially 20 to 400;
b2=0 to 10, preferably 0 to 5, especially 0;
b3=0 to 80, preferably 0 to 50, especially above 0 to 10;
b4=0 to 20, preferably 0 to 10, especially 0;
c1=0 to 30, preferably 1 to 20, especially 2 to 15;
c2=0 to 10, preferably 0 to 5, especially 0;
c3=0 to 10, preferably 0 to 5, especially 0;
c4=0 to 10, preferably 0 to 5, especially 0;
d1=0 to 15, preferably 1 to 12, especially 2 to 10;
with the proviso that
a1+a2+a3+a4>3, preferably >4 and;
a3+b3+c3≥1, preferably >3 and;
c1+c2+c3+c4>1, preferably >2, especially ≥3;
$M=[R^1{}_3SiO_{1/2}]$
$M^A=[R^2R^1{}_2SiO_{1/2}]$
$M^B=[R^3R^1{}_2SiO_{1/2}]$
$M^C=[R^4R^1{}_2SiO_{1/2}]$
$D=[R^1{}_2SiO_{2/2}]$
$D^A=[R^2{}_1R^1{}_1SiO_{2/2}]$
$D^B=[R^3{}_1R^1{}_1SiO_{2/2}]$
$D^C=[R^4{}_1R^1{}_1SiO_{2/2}]$
$T=[R^1SiO_{3/2}]$
$T^A=[R^2SiO_{3/2}]$
$T^B=[R^3SiO_{3/2}]$
$T^C=[R^4SiO_{3/2}]$
$Q=[SiO_{3/2}]$,
$R^1$ independently represents at least one radical from the group of linear, cyclic or branched, aliphatic or aromatic, saturated or unsaturated hydrocarbon radicals having 1 up to 20 carbon atoms,
wherein every $R^1$ more preferably represents methyl,
$R^2$ independently represents a hydrogen, alkoxy, carboxy, hydroxyl or sulphonic ester radical,
preferably a hydrogen radical, an ethoxy radical, a methoxy radical, an acetoxy radical or —O—S(O)$_2$—CF$_3$,
$R^3$ independently represents alike or unalike radicals from the group comprising —CH$_2$—CH$_2$—CH$_2$—O—(CH$_2$—CH$_2$O—)$_x$—(CH$_2$—C(R')$_2$O—)$_y$—(SO)$_z$—R"

—CH$_2$—CH$_2$—O—(CH$_2$—CH$_2$O—)$_x$—(CH$_2$—C(R')$_2$O—)$_y$—R"

where
x=0 to 100, preferably above 0 to 50, especially 1 to 30,
y=0 to 100, preferably 0 to 50, especially above 0 to 29,
z=0 to 100, preferably 0 to 10, especially 0,
with the proviso that x may be alike or unalike y and preferably at least one of the $R^3$ radicals has x being not less than y,
R' in each occurrence is the same or different and independently represents hydrogen and/or a saturated, unsaturated or aromatic hydrocarbon radical having 1 to 12 carbon atoms, optionally substituted with heteroatoms, with alkyl or aryl radicals, with haloalkyl, haloaryl radicals, wherein the heteroatoms are selected from the group containing O, N and/or S and the halogen-containing radicals are preferably para-chlorophenyl or Cl—CH$_2$-radicals, the hydrocarbon radial is more preferably a CH$_2$=CH—CH$_2$—O—CH$_2$-radical or a methyl group and it is especially preferable for the hydrocarbon to be a methyl group,
R" represents a hydrogen radical or an alkyl group of 1 to 4 carbon atoms, a group —C(O)—R''' where R'''=alkyl radical, a group —CH$_2$—O—R', an alkylaryl group, e.g. a benzyl group, the group —C(O)NH—R' or —C(O)O—R', preferably represents hydrogen or methyl,
SO represents a styrene oxide radical —CH(C$_6$H$_5$)—CH$_2$—O— or —CH$_2$—CH(C$_6$H$_5$)—O—,
$R^4$ independently represents alike or unalike radicals from the group of heteroatom-substituted linear, branched or cyclic, saturated, unsaturated or aromatic, optionally heteroatom-interrupted hydrocarbon radicals,
and at least one superplasticizer based on polycarboxylate ethers or sulphonates of lignin, melamine or naphthalene or of resins thereof, preferably a superplasticizer based on polycarboxylate ethers.

Preference is given to compositions of the present invention which comprise at least one organomodified siloxane of formula (I) where the radical
$R^4$ is selected from the group hydroxyalkyl, hydroxyaryl, aminoalkyl, aminoaryl, carboxyalkyl, carboxyaryl, epoxyalkyl, epoxyaryl, chloroalkyl, chloroaryl, fluoroalkyl, cyanoalkyl, alkoxysilyl alkyl, acryloyloxyaryl, acryloyloxyalkyl, methacryloyloxyalkyl, methacryloyloxypropyl or vinyl radicals or radicals having quaternary nitrogen groups and also the radicals

—CH$_2$—CH$_2$—CH$_2$—O—CH$_2$—CH(OH)—CH$_2$OH,

—CH$_2$—CH$_2$—CH$_2$—O—CH$_2$—C(CH$_2$OH)$_2$—CH$_2$—CH$_3$,

[structure: —CH$_2$—CH$_2$—CH$_2$—O—CH$_2$—(epoxide ring)]

[structure: —CH$_2$—CH$_2$—(cyclohexyl fused epoxide)]

[structure: —CH$_2$—CH$_2$—CH$_2$—O—CH$_2$—CH(OH)—CH$_2$—NR$^5{}_2$],

[structure: —CH$_2$—CH$_2$—CH$_2$—O—CH$_2$—CH(NR$^5{}_2$)—CH$_2$—OH],

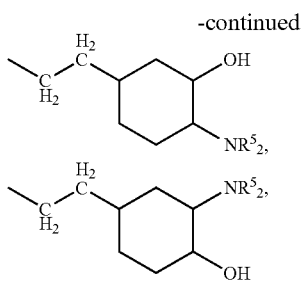

where
R⁵=R¹ and/or hydrogen.

Preference is further given to compositions in accordance with the invention comprising at least one organomodified siloxane of formula (I) wherein, the radicals having quaternary nitrogen groups are selected from the group

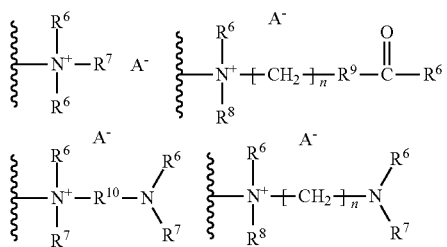

where
$R^6$, $R^7$, $R^8$=each independently represent hydrogen or alkyl radicals having 1 to 30 carbon atoms or radicals of the formula

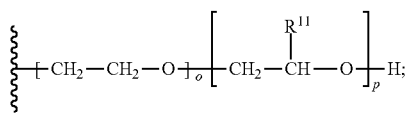

$R^9$ represents identical or different radicals from the group —O—; —NR$^{12}$—;
$R^{10}$ represents identical or different optionally branched divalent hydrocarbon radicals, preferably ethylene or propylene;
$R^{11}$ represents identical or different alkyl, aryl or alkaryl radicals of 1 to 30 carbon atoms, which optionally contain ether functions, preferably methyl, ethyl or phenyl, especially methyl;
$R^{12}$ represents identical or different radicals from the group hydrogen or alkyl of 1 to 6 carbon atoms;
where
n=2 to 18, preferably 3;
o=0 to 30, preferably 0 to 10, especially 1 to 3;
p=0 to 30, preferably 0 to 10, especially 0;
with the proviso that o may be alike or unalike p and preferably o is not less than p, and
$A^-$=identical or different counter-ions to the positive charges on the quaternized nitrogen groups, selected from organic or inorganic anions of the acids HA, and also derivatives thereof.

Preference is further given to compositions comprising one or more siloxanes of formula (I) where any amino-functionality present is in the form of an ionic adduct with protic reactants H⁺A⁻. The adduct is present as a protonated amine with the anion A⁻. The anions A⁻ are identical or different counter-ions to the positive charges on the protonated, primary amino groups selected from organic or inorganic anions of the acids H⁺A⁻, and also derivatives thereof. Preferred anions are, for example, sulphate and hydrogensulphates, carbonate and hydrogencarbonate, acetate and homologous carboxylates with linear or branched, saturated or olefinically unsaturated alkyl chains, aromatic carboxylates, carboxylates formed from amino acids, citrates, malonates, fumarates, maleates, substituted and unsubstituted succinates or carboxylates formed from hydroxy carboxylic acids, for example lactate. The amino-substituted siloxanes of formula (I) and their ionic adducts may be present in dissociation equilibria depending on the stability of the adduct formed.

Where reference is made to natural products, for example lactate, in the context of this invention, this reference is in principle to be understood as meaning all isomers, although the particular naturally occurring isomers are preferred, i.e. the L-lactate in the case mentioned here. As to the definition of natural products, reference is made to the scope of the "Dictionary of Natural Products", Chapman and Hall/CRC Press, Taylor and Francis Group, for example in the online form of 2011: http://dnp.chemnetbase.com/.

The various fragments of the siloxane chains indicated in formula (I) may form a statistical distribution. Statistical distributions may have a blockwise construction with any number of blocks and any sequence or be subject to a randomized distribution, they may also have an alternating construction or else form a gradient along the chain, in particular they can also form any hybrid thereof.

The index numbers reproduced herein and the value ranges of the indices recited can be understood as means of the possible statistical distribution of structures actually present and/or mixtures thereof. This also holds for structural formulae which on the face of it have been reproduced exactly, for example for formula (I) and formula (II).

The word fragment "poly" encompasses in the context of this invention not just compounds having 3 or more repeat units of one or more monomers in the molecule, but especially also compositions of compounds which have a molecular weight distribution and the mean molecular weight of this distribution is at least 200 g/mol. This definition takes account of the fact that it is common practice in the pertinent art to call such compounds polymers even though they do not appear to satisfy a polymer definition as per OECD or REACH guidelines.

The terms alkoxylene and oxyalkylene themselves and also in composita are used interchangeably to denote a divalent radical with one bond being via an oxygen and the other bond via a carbon, while there is at least one carbon atom between these bonding atoms.

GPC measurements to determine the polydispersity and average molar masses are carried out under the following conditions of measurement: column combination SDV 1000/10 000 Å (length 65 cm), temperature 30° C., THF as mobile phase, flow rate 1 ml/min, sample concentration 10 g/l, RI detector, evaluation versus polypropylene glycol standard.

Iodine numbers [g of iodine/100 g of sample] are determined by the method of Hanus, known as method DGF C-V 11 a (53) of the German Society for Fats, and arithmetically converted into the molar masses $MW_{IN}$ for the respective polyethers.

Preference is given to those compositions of the present invention whose siloxanes of formula (I) are characterized in that the radical $R^3$ is selected from a group of at least two different polyethers. Particular preference is given to siloxanes having at least three different radicals $R^3$ of which at least one bears a hydroxyl function at the end of the chain.

Preference is further given to siloxanes in which at least one $R^3$ radical has a molar mass of more than 500 g/mol and preferably of not more than 8000 g/mol.

It is further advantageous for the purposes of the present invention when the polydispersity of the employed polyethers (or to be more precise polyether moieties) $M_w/M_n$ are in the range from 1.0 to 1.5 and their quotients $M_n/MW_{IN}$ and $M_w/MW_{IN}$ are in the range from 0.7 to 1.3, where $MW_{IN}$ is the molecular weight which is known to the person skilled in the art and is calculated from the iodine number.

Preference is further given to compositions of the present invention whose siloxanes of formula (I) satisfy the following conditions: $a3+b3 \neq 0$ and $a4+b4 \neq 0$ where $x \neq 0$ and $y \neq 0$, and wherein $R^4$ is selected from the group comprising (2-triethoxysilyl)-1-ethyl, carboxyalkyl, carboxyaryl, e.g. succinic acid monohexyl ester or phthalic acid monohexyl ester, aminopropyl, (N-aminoethyl)-3-aminopropyl, (N-ethyl)-2-methyl-3-aminopropyl and a radical having a quaternary nitrogen group, for example a trimethylammoniopropyl radical.

Preference is further given to compositions of the present invention whose siloxanes conform to the formula (I) where $a3+b3 \neq 0$ and $R^1$=methyl radical or hydrocarbon radical having more than 10 carbon atoms, wherein the molar ratio of methyl radicals to hydrocarbon radicals having more than 10 carbon atoms is in the range from 10:1 to 100:1.

Preference is further given to compositions of the present invention which comprise siloxanes of formula (I) wherein the weight percentages of siloxane in the organomodified siloxane copolymer are 10-90% by weight, especially 25-75% by weight.

The siloxanes of formula (I) are obtainable in any conceivable manner. Preferably, the siloxanes of formula (I) are prepared as described in DE 10 2008 043343 (US 2010 0113633 A1), DE 10 2009 003274 (US 2010 0298455 A1), DE 10 2007 055485 (US 2010 0249339 A1) or DE 10 2008 041601 (US 2010 0056649 A1), preferably as in DE 10 2008 043343.

In the composition of the present invention, the mass fraction of siloxanes of formula (I) based on total mass fractions of siloxanes and of superplasticizers in the composition is preferably from 0.01 to 10%, preferably from 0.05 to 2% and more preferably from 0.1 to 1%.

The superplasticizers of the type referred to can be any superplasticizer known from the art [Plank, J.: Current Developments on Concrete Admixtures in Europe. In: Proc. Symposium on Chemical Admixtures in Concrete, Dalian (China) 2004.]. The superplasticizers used are preferably polymers of alpha,beta-unsaturated carboxylic acids with polyoxyalkylene sidechains, so-called polycarboxylate ethers. These polycarboxylate ethers have the structure of a comb polymer. The comb polymers are preferably polymers where sidechains are attached to the main chain via ester, amide, imide and/or ether groups. Polycarboxylate ether-based superplasticizers of this type are described in WO2006133933, U.S. Pat. Nos. 6,620,879, 6,211,317, 7,425,596, 6,893,497, 7,238,760, US2002/0019459, U.S. Pat. Nos. 6,267,814, 6,290,770, 6,310,143, 6,187,841, 5,158,996, 6,008,275, 6,136,950, 6,284,867, 5,609,681, 5,494,516; 5,674,929, 5,660,626, 5,668,195, 5,661,206, 5,358,566, 5,162,402, 5,798,425, 5,612,396, 6,063,184, 5,912,284, 5,840,114, 5,753,744, 5,728,207, 5,725,657, 5,703,174, 5,665,158, 5,643,978, 5,633,298, 5,583,183, and 5,393,343. These documents are hereby fully incorporated herein by reference.

Comb-type polycarboxylate ethers of this type can be expressed by formula (II)

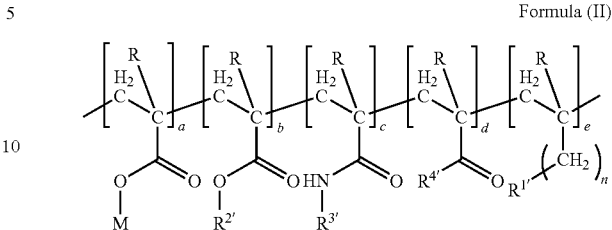

Formula (II)

where the bond attaching group M may vary with the nature of the group M and solvating conditions from covalent to ionic in type, ionically M in each occurrence independently represents $H^+$, alkali metal ion, alkaline earth metal ion, di- or trivalent metal ion, ammonium ion or organic ammonium group n is from 0 to 2, R each independently represents hydrogen or methyl, R' in each occurrence represents an oxyalkylene radical terminally substituted with hydrogen or $R^{5'}$, wherein the alkylene radical is preferably a $C_2$ to $C_{10}$ alkylene and/or alkarylene radical, preferably ethylene, 1,2-propylene, 1,2-butylene or phenylethylene with 2 to 250 repeats, preferably with 8 to 200 repeats and more preferably with 10 to 100 repeats, $R^{2'}$ and $R^{3'}$ each independently represent alkyl, cycloalkyl of 1 to 20 carbon atoms, alkylaryl of 6 to 20 carbon atoms or an oxyalkylene radical terminally substituted with hydrogen or $R^{5'}$, wherein the alkylene radical is a $C_2$ to $C_{10}$ alkylene and/or alkarylene radical, preferably ethylene, 1,2-propylene, 1,2-butylene with 2 to 250 repeats, preferably with 8 to 200 repeats and more preferably with 10 to 100 repeats, $R^{4'}$ in each occurrence independently represents —$NH_2$, —$NR^{6'}R^{7'}$ or —$OR^{8'}NR^{9'}R^{10'}$ where $R^{6'}$ and $R^{7'}$ each independently represent alkyl, cycloalkyl of 1 to 20 carbon atoms or alkylaryl, aryl of 6 to 20 carbon atoms or a hydroxyalkyl group, for example hydroxyethyl, hydroxypropyl, hydroxybutyl, or an acetoxyethyl group ($CH_3$—C(O)—O—$CH_2$—$CH_2$—), hydroxyisopropyl group (HO—CH($CH_3$)—$CH_2$—), acetoxyisopropyl group ($CH_3$—C(O)—O—CH($CH_3$)—$CH_2$—), or $R^{6'}$ and $R^{7'}$ combine to form a ring of which the nitrogen is part in order that a morpholine or imidazoline ring may be constructed, $R^{5'}$ in each occurrence independently represents alkyl, cycloalkyl of 1 to 20 carbon atoms, alkylaryl of 6 to 20 carbon atoms, $R^{8'}$ in each occurrence independently represents a $C_2$ to $C_4$ alkylene group, $R^{9'}$ and $R^{10'}$ each independently represent alkyl, cycloalkyl, hydroxyalkyl of 1 to 20 carbon atoms, alkylaryl of 6 to 20 carbon atoms, wherein the indices a, b, c, d and e represent the molar fraction of the fragments in the comb-type polycarboxylate ether of formula (II), hence the indices a, b, c, d and e sum to 1. It is further preferable for the sum c+d to be above 0.

Preferably, the ratio of the indices a:b:c:d:e is (0.1-0.9):(0.1-0.9):(0-0.8):(0-0.3):(0-0.5).

The fragments with indices a, b, c, d and e of formula (II) may form a statistical distribution. Statistical distributions may have a blockwise construction with any number of blocks and any sequence or be subject to a randomized distribution, they may also have an alternating construction or else form a gradient along the chain, in particular they can also form any hybrid thereof, where groups of different distributions may optionally follow in succession.

The index numbers of formula (II) which are reproduced herein and the value ranges of the indices recited can be understood as means of the possible statistical distribution of structures actually present and/or mixtures thereof.

The polycarboxylate ethers preferably have a molecular weight Mw in the range of 3000-200 000 g/mol, preferably 6000-100 000 g/mol, and more preferably 8000-50 000 g/mol.

Polycarboxylate ethers for the purposes of the present invention are more preferably selected from but not limited to: Mighty 3000S, Mighty 3000H, Mighty 3000R, Mighty 21LV, Mighty 21VS, Mighty 21HF and Mighty 21HP products from Kao Corporation; Aqualock FC600S and FC900 Aqualock products from Nippon Shokubai Co., Ltd.; MalialimAKM-60F, Malialim EKM-60K and Malialim Y-40 products from Nippon Oil & Fats Co., Ltd.; Rehoplus 25, Reobuild SP Serie (8LS, 8LSR, 8N, 8S, 8R, 8SE, 8RE, 8SB-S, 8SB-M, 8SB-L, 8SB-LL, 8HE, 8HR, 8SV, 8RV), Reobuild® range (1000, 1004, 2030, 2424, 860 W1, 888 8000S, 8000E, 8000H), Glenium® range (3030NS, 3400NV, 3000NS, 3200HES, 27, 51, 206, C301, C323, C315), ACE range (ACE28, 30, 32, 38, 40, 48, 68, 327, 329 and ACE338), SKY range (SKY501, 503, 505, 517, 528, 555, 573, 578, 582, 583, 584, 591, 592, 593, 657, 658, 659 and SKY910+), SP-BCR, SP-8CN, SP-8N, 8000, SP-8L) and Melflux® range (1318, 1641, 2453, 2424, 2500, 2510, 2650, 2651 F, 4930, and Meflux 5581) trademarks and products of BASF, BASF Performance Products GmbH, Krieglach, Austria; Sikament® range (Sikament 1200N, 1100NT, 1100NTR, 1100NT-PWR, 1100NT-PSK, 2300, 5370 and Sikament 686), Viscocrete® range (Viscocrete 20 HE, 20 Gold, 111 P, 120 P, 125 P, 225 P, 1020 X, 1035, 1040, 1050, 1051, 1052, 1053, 1055, 1057, 1062, 1063, 1065, 220 HE, 2420, 2500, 2600, 2610, 2620, SC-305, SC-400, 2100, 4100, 6100, 20HE, 3010, 5-500, 5-300, 5 and Viscocrete 20SL), ViscoFlow®-20, Sika GS-1, Sika GS-2, trademarks and products of Sika Deutschland GmbH, Stuttgart, Germany; Muestra range (Muestra 2, Muestra 3), Plastol Ultra 109, product from Euclid Chemical Company, Cleveland, USA; Tuepole HP-8, Tuepole HP-11, Tuepole HP-8R, Tuepole HP-11R, Tuepole HP-11X, Tuepole SSP-104, Tuepole SSP-116, Tuepole HP70, Tuepole NV-G1 and Tuepole NV-G5 products from Takemoto Oil & Fat Co., Ltd.; ADVA® range (ADVA CAST 570, Flow 340, Flow 341, Flow 355, Flow 356, Flow 400, 100 Superplasticizer, ADVA 140, 170, 360, 370, ADVA Cast 500, Cast 530, Cast 540 and ADVA Cast 555 trademarks and products from W. R. Grace Inc., Cambridge, Mass.; Sokalan® range (HP80, 5009X, 5010X, DS3557, R401) trademarks and products of BASF AG; Powerflow range (WR, HWR, SR, SD, WD, WD-K) products from KG Chemical Co., Ltd., Korea; Dynamon series (SP1, SR3), Vibromix series and Mapeifluid series (Mapei) trademarks and products of Mapei S.p.A., Italy; SUPERFLUX® trademarks and of from Axim Concrete Technologies Inc., Middlebranch, Ohio; and Structuro range (Structuro 530, 4020805, 11180, 111X, 290, 100HC, 400X, 285, 402, 335 and Structuro 200), products from AI Gurg Fosroc LLC, Dubai.

The compositions of the present invention may include further ingredients, especially solvents and binders. By way of solvents, the composition of the present invention may more particularly include water or mono- or polyhydric monomeric, oligomeric or polymeric alcohols such as ethylene glycol, propylene glycol, butyldiglycol, dipropylene glycol, polyethylene glycol or polypropylene glycol. The composition of the present invention preferably includes sufficient solvent for the mass ratio of solvent to siloxanes of formula (I) to be in the range from 0.1:1 to 100:1, preferably in the range from 0.2:1 to 20:1 and more preferably in the range from 0.3:1 to 10:1.

The composition of the present invention may include any binder known in the building construction industry for example. The composition of the present invention may include one or more of these binders. Preferred binders are selected from cement and binders comprising calcium sulphate (or forms thereof with water of crystallization), such as gypsum for example. Preferred binders are cement or gypsum, more preferably cement.

Any known cement can be used. The cement used preferably contains at least a calcium silicate, aluminate and/or ferrite. Preference is given to using Portland cement (CEM I), Portland composite cement (CEM II), blast furnace cement (CEM III), pozzolanic cement (CEM IV) and composite cement (CEM V) or high-alumina cement, as described in the literature (Zement, Grundlagen der Herstellung and Verwendung, Verlag Bau+Technik, 2000). The composition preferably includes sand as a further aggregate. The sand preferably has a maximum particle size of 4 mm. The particle size can be determined by simple sieving.

In addition to or in place of sand, preferably in addition to sand, the composition of the present invention may also include gravel. The gravel used preferably has a minimum particle size of above 4 mm.

Further suitable aggregates for inclusion in the compositions of the present invention are discernible for example from Römpp Chemielexikon, Georg Thieme Verlag, 2011 under the headword of Betonzuschlag (document identifier RD-02-01140).

The mass ratio of aggregates to the mixture of superplasticizer and siloxanes of formula (I) is preferably in the range from 10:1 to 100 000:1, more preferably in the range from 20:1 to 10 000:1 and even more preferably in the range from 100:1 to 1000:1.

Further constituents of hydrophilic defoamer compositions according to the present invention may be retarders such as gluconates, tartrates or phosphonates, accelerators such as lithium carbonate, anti-shrinkage additives such as mono- or polyhydric alcohols, preservatives, pigments such as titanium dioxide or organic pigments, anti-freeze agents such as chlorides, polymers such as acrylates, additives for internal after-treatment, organic and inorganic thickeners such as starch or bentonite, hydrophobicizers such as silanes, siloxanes, silicone oils or salts of fatty acids.

The compositions of the present invention are obtainable by simply mixing, preferably under agitation. The process for producing the compositions of the present invention can be a batch process or a continuous process. The composition is preferably obtained at a temperature of 0° C. to 130° C., preferably 5° C. to 60° C. and more preferably at the particular outside temperature at the site of production.

The composition of the present invention may be, for example, a building-product mixture, preferably a mortar or concrete mixture. This is particularly the case when the composition of the present invention comprise cement and/or calcium sulphate (or its form with water of crystallization) binders with or without one or more aggregates.

The compositions of the present invention or the siloxanes of formula (I) as described above can be used as or for production of building-product mixtures or building products, especially mortar mixtures or concrete mixtures. The building-product mixtures can be used for production of mortars or concrete. The present invention accordingly also provides building products or building-product mixtures, especially mortar mixtures, concrete mixtures or ready-produced parts, preferably ready-produced parts, for example ready-produced concrete parts or gypsumboard produced using a composition of the present invention, or corresponding building products and ready-produced parts comprising the compositions of the present invention.

Having generally described this invention, a further understanding can be obtained by reference to certain specific examples which are provided herein for purposes of illustration only and are not intended to be limiting unless otherwise specified.

EXAMPLES

Example 1

Preparation of Polyether Siloxanes

Polyethers Used

The polyethers were prepared in accordance with the familiar prior art methods, as described in EP2182020 and the references cited therein. Molecular weights $M_n$ and $M_w$, were determined by gel permeation chromatography under the following conditions of measurement: column combination SDV 1000/10 000 Å (length 65 cm), temperature 30° C., THF as mobile phase, flow rate 1 ml/min, sample concentration 10 g/l, RI detector, evaluation versus polypropylene glycol standard (76 to 60 000 g/mol).

Iodine numbers [g of iodine/100 g of sample] were determined by the method of Hanus, known as method DGF C-V 11 a (53) of the German Society for Fats, and arithmetically converted into the molar masses $MW_{IN}$ for the respective polyethers.

Polyethers of the Formula

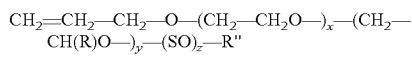

$$CH_2=CH_2-CH_2-O-(CH_2-CH_2O-)_x-(CH_2-CH(R)O-)_y-(SO)_z-R''$$

which are used according to the present invention are
PE1a: R'=CH$_3$, R''=H, z=0, x=14, y=3.73,
  $MW_{IN}$=893.7 g/mol, Mn=798 g/mol, Mw=874 g/mol
PE1b: R'=CH$_3$, R''=CH$_3$, z=0, x=14, y=3.73,
  $MW_{IN}$=860.4 g/mol, Mn=817 g/mol, Mw=880 g/mol
PE2a: =CH$_3$, R''=H, z=0, x=13.6, y=14.2,
  $MW_{IN}$=1410.1 g/mol, Mn=1266 g/mol, Mw=1368 g/mol
PE2b: R'=CH$_3$, R''=CH$_3$, z=0, x=13.6, y=14.2,
  $MW_{IN}$ 1458.7=Mn=1260 g/mol, Mw=1383 g/mol
PE2c: R'=CH$_3$, R''=CH$_3$, z=0, x=13.6, y=14.2,
  $MW_{IN}$ 1492.3=g/mol, Mn=1261 g/mol, Mw=1378 g/mol
PE3a: R'=CH$_3$, R''=H, z=0, x=41, y=43,
  $MW_{IN}$=4532.3 g/mol, Mn=3500 g/mol, Mw=4315 g/mol
PE3b: R'=CH$_3$, R''=H, z=0, x=37, y=39,
  $MW_{IN}$=3845.5 g/mol, Mn=2844 g/mol, Mw=3727 g/mol
PE3c: R'=CH$_3$, R''=CH$_3$, z=0, x=37, y=39,
  $MW_{IN}$ 3678.4=g/mol, Mn=2891 g/mol, Mw=3617 g/mol
PE3d R'=CH$_3$, R''=CH$_3$, z=0, x=37, y=39,
  $MW_{IN}$ 3788.1=g/mol, Mn=2918 g/mol, Mw=3634 g/mol Hydrosiloxanes Used According to the Present Invention:

The hydrosiloxanes were prepared as described in Example 1 of EP 1439200 B1. The hydrosiloxanes used are defined as per the following formula:

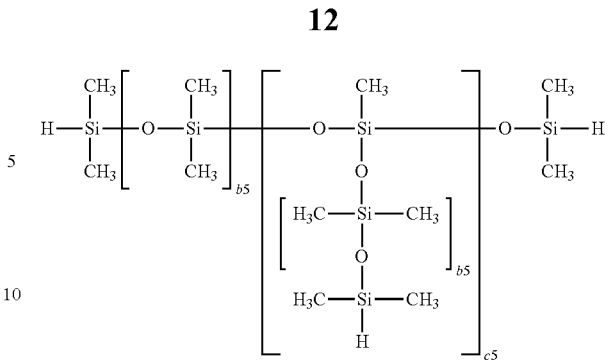

where
b5=1 to 600, preferably 10 to 500, especially 20 to 400, and
c5=0 to 30, preferably 1 to 20, especially 2 to 15.
SIL1: b5=68, c5=5; 1.17 of SiH equivalents/kg
SIL2: b5=350, c5=5; 0.24 of SiH equivalents/kg
SIL3: b5=74, c5=7; 1.32 of SiH equivalents/kg Polyether Siloxanes Used According to the Present Invention:

The polyether siloxanes in table 1 were prepared as described in Example 7 of WO 2009/065644 by using the starting weights of table 1.

TABLE 1

Starting weights to prepare the polyether siloxanes used according to the invention, as per Example 1

| Synthesis example | Siloxane starting weight | Starting weights of individual polyethers | | |
|---|---|---|---|---|
| S1 | 51.6 g SIL1 | 25.3 g PE1b | 23.6 g PE2b | 134.0 g PE3c |
| S2 | 51.6 g SIL1 | 25.3 g PE1b | 23.6 g PE2b | 165.2 g PE3a |
| S3 | 144.5 g SIL2 | 14.7 g PE1b | 13.8 g PE2b | 78.2 g PE3c |
| S4 | 114.6 g SIL3 | 61.1 g PE1b | 58.3 g PE2c | 332.7 g PE3d |
| S5 | 114.6 g SIL3 | 58.8 g PE1a | 55.05 g PE2a | 337.78 g PE3b |

Example 2

Compositions

The compositions of the present invention were produced by combining appropriate amounts at room temperature and briefly stirring, swirling or shaking.

TABLE 2

Inventive compositions comprising at least one inventive siloxane and at least one superplasticizer based on polycarboxylate ethers, the numbers indicate the fraction of the composition which is accounted for by the siloxane, in % by weight.

| Superplasticizer | Inventive siloxane | | | | |
| | S1 | S2 | S3 | S4 | S5 |
|---|---|---|---|---|---|
| Sika GS-1 | 0.3 | 0.3 | 0.3 | 0.3 | 0.3 |
| Meflux 1318 | 0.2 | 0.4 | 0.4 | 0.2 | 0.4 |
| Rheoplus 25 | 0.8 | 0.8 | 0.8 | 0.8 | 0.8 |
| Sika GS-2 | 0.25 | 0.25 | 0.3 | 0.3 | 0.3 |
| Plastol Ultra 109 | 0.4 | 0.15 | 0.15 | 0.15 | 0.4 |
| Dynamon SP1 | 0.1 | 0.1 | 0.3 | 0.3 | 0.3 |
| Meflux 2500 | 0.25 | 0.25 | 0.25 | 0.5 | 0.5 |
| Muestra 3 | 0.25 | 0.25 | 0.15 | 0.15 | 0.15 |
| Viscocrete1053 | 0.35 | 0.35 | 0.35 | 0.25 | 0.25 |
| Dynamon SR3 | 0.5 | 0.5 | 0.3 | 0.3 | 0.3 |
| Muestra 2 | 0.2 | 0.2 | 0.66 | 0.66 | 0.66 |

The product BASF MVA 2500 L has been replaced by BASF with BASF Meflux 2500.

Example 3

Using the Compositions

The defoamers used in the examples are given in table 3. Defoamers E1 to E5 are siloxanes of formula (I).

TABLE 3

Defoamers used

| Defoamer | | |
|---|---|---|
| E1 | Synthesis Example S1 | inventive |
| E2 | Synthesis Example S2 | inventive |
| E3 | Synthesis Example S3 | inventive |
| E4 | Synthesis Example S4 | inventive |
| E5 | Synthesis Example S5 | inventive |
| E6 | Tego Antifoam MR 2132, Evonik Industries AG | not inventive without addition of E1-E5 |
| E7 | Tego IS 9520, Evonik Industries AG | not inventive without addition of E1-E5 |
| E8 | Tego IS 9500, Evonik Industries AG | not inventive without addition of E1-E5 |

Example 3a

Solubility Testing of Defoamers

The defoamers were tested for solubility in water and also in superplasticizers based on polycarboxylate ethers. The components were stirred at room temperature in the respective mass-percentage proportions into water or, respectively, the superplasticizer without special shearing in the sample jar with a laboratory magnetic stirrer from IKA. Defoamer components were considered insoluble if they, after the stirrer had been switched off, separated from the polar phase or are not even emulsified in the first place. The results are reported in table 4.

TABLE 4

Water solubility of defoamer components at room temperature as per Example 3a

| Sample | 2 g/30 g (6.25% by wt. strength): | 10% strength | 20% strength | 30% strength |
|---|---|---|---|---|
| E1 | soluble (clear) | soluble (clear) | soluble (clear) | soluble (clear) |
| E6 | visible phase separation after 10 min | / | / | / |
| E7 | visible phase separation after 10 min | / | / | / |

Defoamers E6 and E7, being non-inventive defoamers, prove to be water-insoluble.

TABLE 5

Solubility of defoamers in superplasticizers at room temperature (23° C.) as per Example 3a

| Sample | Superplasticizer | Solubility in superplasticizer at 0.4% by weight |
|---|---|---|
| E1 | Sika ® ViscoCrete ®-1051 | soluble (clear) |
| E6 | Sika ® ViscoCrete ®-1051 | visible phase separation after 10 min |
| E7 | Sika ® ViscoCrete ®-1051 | visible phase separation after 10 min |

TABLE 5-continued

Solubility of defoamers in superplasticizers at room temperature (23° C.) as per Example 3a

| Sample | Superplasticizer | Solubility in superplasticizer at 0.4% by weight |
|---|---|---|
| E1 | BASF MVA 2500 L | soluble (cloudy) |
| E6 | BASF MVA 2500 L | visible phase separation after 10 min |
| E7 | BASF MVA 2500 L | visible phase separation after 10 min |

All the aqueous solutions (table 4) and superplasticizer blends (table 5) were intensively shaken by hand for 15 seconds in a 50 ml screw top glass to allow visual assessment of the foaming behaviour. In all cases, foam formation was distinctly reduced compared with the blank value and, what is more, very rapid degradation of the foam could be observed.

Example 3b

Producing a Mortar Material for Determining Air Content and Slump in Line with DIN 18555 Part 2

The pulverulent components of the mortar mixture were weighed into the stirring pot of a Hobart mixer. The pot was secured to the Hobart mixer. A moist tissue cloth was placed on the protective grid to reduce dust. The dry mixture was subsequently mixed for two minutes at stirrer setting 1. The liquid additives were added to the mixing water and this mixture was added at the same stirrer setting (setting 1) to the dry mixture and subsequently stirred in for two minutes.

To achieve higher entrapment of air, the following procedure was subsequently adopted: The stirrer motor was initially switched off. Any sediment (if present) was stirred up by hand and the stirrer setting was subsequently raised to setting 2. The stirrer was restarted and the mixture was commixed on the higher stirrer setting for two minutes.

The components used and their proportions are reported in table 6.

Example 3c

Determining the Percentage Air Content and the Slump on the Tamping Table in Line with DIN 18555 Part 2

The ready-mixed mortar from Example 2 was introduced into the container of the air pore measuring instrument (of the Testing type, serial number 2558, manufacturer: tecnotest, IT) and smoothed down; the rest was kept for determining the slump. Then, the upper part of the instrument was added, the instrument was sealed and filled with distilled water. Then, air was pumped into the upper part of the container and the pressure was adjusted such that the scale indicator points to the zero line. The system was depressurized via a valve and the air content (in % by volume) was read off from the display.

The rest of the mortar mixture was introduced into the mould on the slump table and again smoothed down (mould must be filled correctly). Then, the mould was lifted off the slump table and the crank on the slump instrument was turned 15× within 10 seconds; each turn of the crank resulted by virtue of the screw-shaped construction in a tapping operation which leads to the mortar mix spreading out.

After the operation, the diameter of the spread-out "cake" was measured with a ruler along two mutually perpendicular axes and averaged.

The measured results are reported in table 6 and show that adding a PCE superplasticizer to a mortar mixture consisting of sand, cement and water improves the flowability—as measured by the slump (diameter of mortar sample in mm), but also increases the entrapped air—as measured by the air content (in % by volume).

Adding defoamers reduces the air content. Particularly the inventive compositions comprising a siloxane of formula (I) and a PCE superplasticizer display an advantageous behaviour with regard to air content, flowability and compatibility of the inventive composition in contrast to non-inventive compositions.

The sand used was a standard sand to EN196-1 from Normensand GmbH, Beckum. The cement used was a Portland cement from Phoenix (RM CEM 142.5R). The superplasticizers used were MVA 2500 L from BASF SE (new designation: Meflux 2500) and Viscocrete 1053 from Sika.

TABLE 6

Compositions and test results of measured mortar mixes as per Example 3c

| Starting weights: | Amount [g] | Air content [vol %] | slump [mm] | Amount [g] | Air content [vol %] | slump [mm] |
|---|---|---|---|---|---|---|
| Sand | 2700 | | | 2700 | | |
| Cement | 900 | | | 900 | | |
| Water | 405 | | | 360 | | |
| Without superplasticizer | | 5.0 | 125 | | | |
| BASF superplasticizer | 4.50 | 19.0 | 270 | 4.50 | 17.0 | 118 |
| With superplasticizer and with defoamer | | | | | | |
| E8 | | | | 0.0113 | 6.5 | 150 |
| Triisobutyl phosphate | | | | 0.0113 | 7.8 | 150 |
| E1 | 0.0113 | 8.5 | 294 | 0.0113 | 8.5 | 155 |
| E2 | | | | 0.0113 | 7.0 | 147 |
| E3 | | | | 0.0113 | 6.0 | 150 |

| Starting weights | Amount [g] | Air content [vol %] | slump [mm] | Appearance |
|---|---|---|---|---|
| Sand | 2700 | | | |
| Cement | 900 | | | |
| Water | 405 | | | |
| Without superplasticizer | | 5.0 | 125 | clear, homogeneous |
| Sika superplasticizer | 4.50 | 25.0 | 220 | clear, homogeneous |
| With superplasticizer and with defoamer | | | | |
| E8 | 0.0113 | 7.5 | 178 | cloudy, homogeneous |
| E4 | 0.0113 | 17.0 | 195 | cloudy, homogeneous |
| E5 | 0.0113 | 16.5 | 190 | cloudy, homogeneous |
| E8/E4; blend (1:1) | 0.0113 | 8.0 | 178 | slightly cloudy, homogeneous |
| E8/E5 blend (1:1) | 0.0113 | 8.0 | 174 | slightly cloudy, homogeneous |

Appearance was assessed for the pure superplasticizer and the mixtures of the stated amounts of defoamer and superplasticizer after three days rest at room temperature.

Obviously, numerous modifications and variations of the present invention are possible in light of the above teachings. It is therefore to be understood that within the scope of the appended claims, the invention may be practiced otherwise than as specifically described herein.

This application is based on German patent application DE 10 2011 089 535.3 filed in the German Patent Office on Dec. 22, 2011, the entire contents of which are hereby incorporated by reference.

What is claimed as new and desired to be secured by Letters Patent of the United States is:

1. Composition comprising at least one siloxane of the formula (I)

$$M_{a1}M^A_{a2}M^B_{a3}M^C_{a4}D_{b1}D^A_{b2}D^B_{b3}D^C_{b4}T_{c1}T^A_{c2}T^B_{c3}T^C_{c4}Q_{d1} \quad \text{(Formula I)}$$

where
a1=0 to 32,
a2=0 to 10,
a3=0 to 32,
a4=0 to 10,
b1=1 to 600,
b2=0 to 10,
b3=0 to 80,
b4=0 to 20,
c1=0 to 30,
c2=0 to 10,
c3=0 to 10,
c4=0 to 10,
d1=0 to 15,
with the proviso that
a1+a2+a3+a4>3, and;
a3+b3+c3≥1, and;
c1+c2+c3+c4>1,
$M=[R^1_3SiO_{1/2}]$
$M^A=[R^2R^1_2SiO_{1/2}]$
$M^B=[R^3R^1_2SiO_{1/2}]$
$M^C=[R^4R^1_2SiO_{1/2}]$
$D=[R^1_2SiO_{2/2}]$
$D^A=[R^2_1R^1_1SiO_{2/2}]$
$D^B=[R^3_1R^1_1SiO_{2/2}]$ $D^C=[R^4{}_1R^1{}_1SiO_{2/2}]$
$T=[R^1SiO_{3/2}]$
$T^A=[R^2SiO_{3/2}]$
$T^B=[R^3SiO_{3/2}]$
$T^C=[R^4SiO_{3/2}]$
$Q=[SiO_{4/2}]$, $R^1$ independently represents at least one radical from the group of linear, cyclic or branched, aliphatic or aromatic, saturated or unsaturated hydrocarbon radicals having 1 up to 20 carbon atoms, $R^2$ independently represents a hydrogen, alkoxy, carboxy, hydroxyl or sulphonic ester radical, $R^3$ independently represents alike or unalike radicals from the group comprising

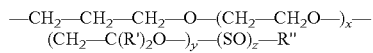

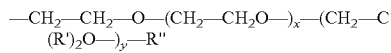

where
x=0 to 100,
y=0 to 100,
z=0 to 100,
with the proviso that x may be alike or unalike y, R' in each occurrence is the same or different and independently represents hydrogen and/or a saturated, unsaturated or aromatic hydrocarbon radical having 1 to 12 carbon atoms, optionally substituted with heteroatoms, with alkyl or aryl radicals, with haloalkyl, haloaryl radicals, wherein the heteroatoms are selected from the group consisting of O, N and/or S, R" represents a hydrogen radical or an alkyl group of 1 to 4 carbon atoms, a group —C(O)—R'" where R'"=alkyl radical, a group —CH$_2$—O—R', an alkylaryl group, e.g. a benzyl group, the group —C(O)NH—R' or —C(O)O—R', SO represents a styrene oxide radical —CH(C$_6$H$_5$)—CH$_2$—O—, $R^4$ independently represents alike or unalike radicals from the group of heteroatom-substituted linear, branched or cyclic, saturated, unsaturated or aromatic, optionally heteroatom-interrupted hydrocarbon radicals, and at least one superplasticizer based on polycarboxylate ethers or sulphonates of lignin, melamine or naphthalene or of resins thereof, wherein said at least one siloxane comprises at least two different polyalkoxylene moieties, wherein a 6.25 wt. % of said at least one siloxane of the formula (I) in water is clear at room temperature.

2. The composition according to claim 1, wherein $R^4$ is selected from the group hydroxyalkyl, hydroxyaryl, aminoalkyl, aminoaryl, carboxyalkyl, carboxyaryl, epoxyalkyl, epoxyaryl, chloroalkyl, chloroaryl, fluoroalkyl, cyanoalkyl, alkoxysilylalkyl, acryloyloxyaryl, acryloyloxyalkyl, methacryloyloxyalkyl, methacryloyloxypropyl or vinyl radicals or radicals having quaternary nitrogen groups and also the radicals

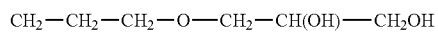

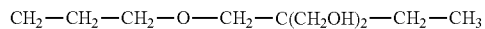

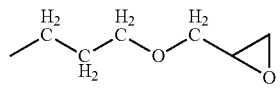

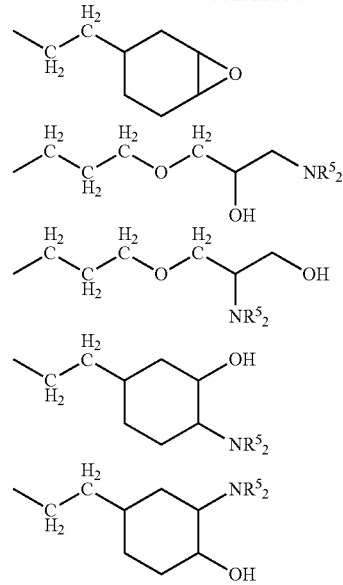

where
$R^5=R^1$ and/or hydrogen.

3. The composition according to claim 2, wherein $R^4$ are radicals having quaternary nitrogen groups and said radicals having quaternary nitrogen groups are selected from the group

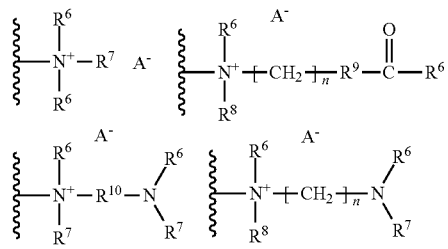

where
$R^6$, $R^7$, $R^8$=each independently represent hydrogen or alkyl radicals having 1 to 30 carbon atoms or radicals of the formula

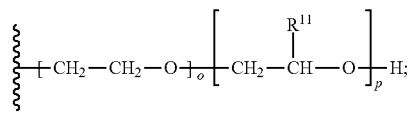

$R^9$ represents identical or different radicals from the group —O—; —NR$^{12}$—;

$R^{10}$ represents identical or different optionally branched divalent hydrocarbon radicals;

$R^{11}$ represents identical or different alkyl, aryl or alkaryl radicals of 1 to 30 carbon atoms, which optionally contain ether functions;

$R^{12}$ represents identical or different radicals from the group hydrogen or alkyl of 1 to 6 carbon atoms;

where
n=2 to 18,
o=0 to 30,
p=0 to 30,
with the proviso that o may be alike or unalike p,
and
A⁻=identical or different counter-ions to the positive charges on the quaternized nitrogen groups, selected from organic or inorganic anions of the acids HA, and also derivatives thereof.

4. The composition according to claim 1, wherein a mass fraction of siloxanes of formula (I) based on a total mass fractions of siloxanes of formula (I) and of superplasticizers is from 0.01 to 10%.

5. The composition according to claim 1, further comprising a binder.

6. The composition according to claim 5, wherein said composition is a building-product mixture.

7. The composition according to claim 6, wherein said building-product mixture is at least one of a mortar mixture or a concrete mixture.

8. A method of preparing a building-product mixture comprising adding the composition according to claim 1 to a binder.

9. The composition according to claim 1, wherein
R³ independently represents alike or unalike radicals from the group comprising

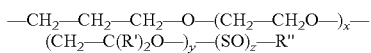

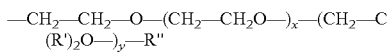

where
x=0 to 100,
y=0 to 100,
z=0 to 100,
with the proviso that x may be alike or unalike y and at least one of the R³ radicals has x being not less than y.

10. The composition according to claim 1, wherein R' is substituted with at least one of a haloalky radical and haloaryl radical selected from the group consisting of para-hlorophenyl or Cl—CH₂— radicals.

11. The composition according to claim 1, wherein R' is a hydrocarbon radial selected from the group consisting of a CH₂=CH—CH₂—O—CH₂— radical and a methyl group.

12. The composition according to claim 3, wherein $R^{10}$ represents ethylene or propylene.

13. The composition according to claim 3, wherein $R^{13}$ represents methyl, ethyl or phenyl, especially methyl.

14. The composition according to claim 3, wherein $R^{13}$ represents methyl.

15. The composition according to claim 3, wherein o is not less than p.

16. The composition according to claim 5, wherein said binder is at least one binder selected from the group consisting of calcium sulphate and cement.

17. The composition according to claim 1, further comprising water.

18. The composition according to claim 5, further comprising sand.

19. A method of defoaming a building-product mixture comprising a binder and a superplasticizer comprising adding at least one siloxane of the formula (I)

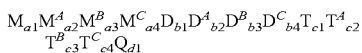
(Formula I)

where
a1=0 to 32,
a2=0 to 10,
a3=0 to 32,
a4=0 to 10,
b1=1 to 600,
b2=0 to 10,
b3=0 to 80,
b4=0 to 20,
c1=0 to 30,
c2=0 to 10,
c3=0 to 10,
c4=0 to 10,
d1=0 to 15,
with the proviso that
a1+a2+a3+a4>3, and;
a3+b3+c3≥1, and;
c1+c2+c3+c4>1,
$M=[R^1{}_3SiO_{1/2}]$
$M^A=[R^2R^1{}_2SiO_{1/2}]$
$M^B=[R^3R^1{}_2SiO_{1/2}]$
$M^C=[R^4R^1{}_2SiO_{1/2}]$
$D=[R^1{}_2SiO_{2/2}]$
$D^A=[R^2{}_1R^1{}_1SiO_{2/2}]$
$D^B=[R^3{}_1R^1{}_1SiO_{2/2}]$
$D^C=[R^4{}_1R^1{}_1SiO_{2/2}]$
$T=[R^1SiO_{3/2}]$
$T^A=[R^2SiO_{3/2}]$
$T^B=[R^3SiO_{3/2}]$
$T^C=[R^4SiO_{3/2}]$
$Q=[SiO_{4/2}]$,
R¹ independently represents at least one radical from the group of linear, cyclic or branched, aliphatic or aromatic, saturated or unsaturated hydrocarbon radicals having 1 up to 20 carbon atoms,
R² independently represents a hydrogen, alkoxy, carboxy, hydroxyl or sulphonic ester radical,
R³ independently represents alike or unalike radicals from the group comprising

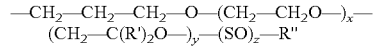

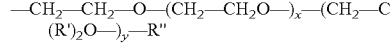

where
x=0 to 100,
y=0 to 100,
z=0 to 100,
with the proviso that x may be alike or unalike y,
R' in each occurrence is the same or different and independently represents hydrogen and/or a saturated, unsaturated or aromatic hydrocarbon radical having 1 to 12 carbon atoms, optionally substituted with heteroatoms, with alkyl or aryl radicals, with haloalkyl, haloaryl radicals, wherein the heteroatoms are selected from the group consisting of O, N and/or S,
R" represents a hydrogen radical or an alkyl group of 1 to 4 carbon atoms, a group —C(O)—R'" where R'"=alkyl radical, a group —CH₂—O—R', an alkylaryl group, e.g. a benzyl group, the group —C(O) NH—R' or —C(O)0—R',
SO represents a styrene oxide radical —CH(C₆H₅)—CH₂—O—,
R⁴ independently represents alike or unalike radicals from the group of heteroatom-substituted linear, branched or cyclic, saturated, unsaturated or aromatic, optionally heteroatom-interrupted hydrocarbon radicals, and at least one superplasticizer based on polycarboxylate ethers or sulphonates of lignin, melamine or naphthalene or of resins thereof, wherein said at least one siloxane comprises at least two different polyalkoxylene moieties, wherein a 6.25 wt. % of said at least one siloxane of the formula (I) in water is clear at room temperature.

20. The composition according to claim 1, wherein a 30 wt. % of said at least one siloxane of the formula (I) in water is clear at room temperature.

* * * * *